(12) United States Patent
Shorrosh et al.

(10) Patent No.: US 7,750,139 B2
(45) Date of Patent: Jul. 6, 2010

(54) NUCLEIC ACIDS FROM SESAME PLANTS

(75) Inventors: Basil S. Shorrosh, Ft. Collins, CO (US); Matthew Jenkin, Johnstown, CO (US); Benyuan Dang, Ft. Collins, CO (US)

(73) Assignee: Cargill, Incorporated, Wayzata, MN (US)

( * ) Notice: Subject to any disclaimer, the term of this patent is extended or adjusted under 35 U.S.C. 154(b) by 185 days.

(21) Appl. No.: 10/565,898

(22) PCT Filed: Jul. 29, 2004

(86) PCT No.: PCT/US2004/024858

§ 371 (c)(1),
(2), (4) Date: Jan. 25, 2006

(87) PCT Pub. No.: WO2005/012496

PCT Pub. Date: Feb. 10, 2005

(65) Prior Publication Data

US 2006/0160217 A1    Jul. 20, 2006

Related U.S. Application Data

(60) Provisional application No. 60/490,873, filed on Jul. 29, 2003.

(51) Int. Cl.
C07H 21/04    (2006.01)
C12N 15/82    (2006.01)
C12N 5/10    (2006.01)

(52) U.S. Cl. .................. 536/24.1; 435/320.1; 435/419; 435/468; 800/278

(58) Field of Classification Search .................. None
See application file for complete search history.

(56) References Cited

FOREIGN PATENT DOCUMENTS

EP            0 723 019 A1    7/1996
WO        WO 03/052111        6/2003

OTHER PUBLICATIONS

Roeckel, P. et al. "Effects of seed-specific expression of a cytokinin biosynthetic gene on canola and tobacco phenotypes". *Transgenic Research*, 6, 133-141 (1997).

Sunilkumar, G. et al. "Cotton a-globulin promoter: isolation and functional characterization in transgenic cotton, *Arabidopsis*, and tobacco". *Transgenic Research*, 11, 347-359 (2002).

Tai et al., "Expression Pattern and Deposition of Three Storage Proteins, 11S Globulin, 2S Albumin and 7S Globulin in Maturing Sesame Seeds," *Plant Physiol. Biochem*, 2001, 39: 981-992.

*Primary Examiner*—Ashwin Mehta

(57) ABSTRACT

Novel nucleic acids derived from the 5' untranslated regions of the 2S albumin and 11S globulin genes from sesame are disclosed. These novel nucleic acids can be used to direct expression of coding nucleic acids. Expression constructs can be introduced into a plant cell to generate a transgenic plant cell or to generate a transgenic plant.

12 Claims, 3 Drawing Sheets

Figure 1

Sesame 2S Albumin 5'UTR Region (SEQ ID NO:1)

CTGAAATCATGTGAACTCATAAAATGATTTAAGAAAAATGAAACTAATAAGAAGATATCCAT
ATGTRTGCCGGCATTAACACTGTTCGGTGAAAGGAATTGGAGAAGAAGGAAARAGAATATAA
TTCATTGGTGAAGAAAATAATGAGGAAACAAGTTCCACGTGGAAAAGAAAATAAAAAGAATA
TCCGCGAAACTTTAAATTTACGGCTGAAGAAAACCTGAGATCAGAAATCTCGTGTGGAAAGT
GCCGCTCATCGCACCACCGGAATTATTTCCCGGCCGATGCTGCGTCTGCACATAGCTGAGAT
TATCATCATTCCATAGCTTTCATCATCAACGGAAAGAAATATTGAAAAGAATCGACTTTGG
TGAAAAAACAACACACGATACGAAGCAATAATACATATGACTATAAATCAAAATTCACATAT
GACGGACAGTTCTACAGAACAAAAAGGAATATGTAGCCTTGGAGGCAAGTCGCAGAAAAGGC
GATGTTAATGCCAGAGTTCCACTCTGCCGTTCTTGACGGCATAATTGAAGATTGAAAGGGCT
TTTATAATAATGTTGGCCGTTGCCCTAATTCCCAAATGGGCGCCCGCACCGCTGTTTGGATT
CAGAATCCCAATGGGAACTTCTTTCTTTTTTTCCCCTCTATTTTTTGTAGTTCTCCCATTTG
AGAAGAAAATGATAAGTTACATCCCGTAAGTTAATTTTTTTTATGATTTTAGTGTCCTTGTA
TTTTAATTCACCACATTGCATTTATAATTTTGAAAACTTTtATTTTAGTTCAAAATCTTTA
ATATCGTTAAGTTTTTtATAAAAACGACTCGTGTATGAAATGCTCTTCCTTAAGTTTTGAGG
GGAATGAAAGTTGTTTTTGCTAGAAATTAAATAAAACTAAGACTTGATATTGAAATTATAAT
TTTCTTGAAGTTATATTATACACTGTGGCGAGTTAAAAAATAATAAAATCAAAATGACGAAG
ATGCTAACTTATGGGATGTAAATGCAATTCTTTCATATTAATGCAAACTGTAAATATTGCAC
AAATCTCTGTGTCGGTTCACCTATAATGTGTTGAAACTTTAAAATATTATATTTATTTTATT
GAATTCCTAATCAAACAAATTTGGTATAATCAATGGCTCGTTCCAAACACAATCACTCTGTT
AGATATATTTTGAAACCTAGAAAAGTATATTTTTCTTTATAATAGATATTATAGATAACAAA
CTATAAGTTTCAGAATAATGCTAGTAGTAGTGGTGATTACCAAATCTGAATATGAAGATAGA
ACTATATTTGCAACATAATTTTGATAGTATAAAATTATATTCATGACAAAGTCTTAGGAGTT
TCATTTATTTGATTTGGGAGTTCAATTACAAATAACAAGTGAGGAGGGGTGTGATGAATGG
ATCAAATTTGGGTTGTTGTTGGGCTCCATCCACTTGAAACCCTGTCATCCATTCTATTGACC
TTTTGAAGTGATTGTAGTTGTTGTGCTTTAGTAGGCACTTATCACATGCCATTGAGTTCAAA
AAGAGAAAAATTGCGTCACATGTTGTCCATGTCTACAATGCTTTTATAAGCTAAATTGAATG
GGTTGATAAACAAGTTAGACTAGAAATTAATGGATTTTTCCTTTCGTTTTATAGGGGATTGA
ATTTTCTATTGTATATTACTTTTATGAGTATAATTTGTCTTTGAAATAAATTAGGTAATGTA
ATATTTGTAGTTATGTTAAATGAAATAAAAGATATAATAATCTTTAAAATAATTTTTTTGCT
TATGTTGTTAATGATGCAACTTTATTCTTCTTTTTTATAAGCACACACCCAATTCAAACCC
AAGATCTTTGATATGCAGTTTTGAGCCCAAACTGTGGAACTGTCCTTGGAGCTAAAGATGCA
TCAAGGGAACTTAAACAAGAGTTAGAGGTATAATTGTTGAGTTGTAATATGCTAATAACTCA
TTATTTTAGTTTGTCTCCTCCATGGATAAGGATGTCTTTTATGACCAGCTCAATTTCTGTTA
ATTGGCCATTAAAGTTTCCTTTAGCACTRGTTCAGACACTTACGAGAAAGAGAAACATTTTG
TGTTAGAGGAACTAATATTAATTAAACTAGATCCAAAAGAGAAGTTCTAAAAAATTCAAGTC
CTCTGTTTTGGCAACATCTGCATGTAGACATCGATGTGGAAGCTCGAAAACGCCAGCCTCAG
TCCCCTCAGCAAAACCCGTCCAĊCTATCTCTTCCATCAATCAACACGTAAAAGCCATGCACC
CGCACAAAACCACTATAAATCCCCCTTCAAACCCCTCCACCATTCTCACACCACTGTAAACT
CATCTACTCCTTTCCTACATATAAATCTCAGTTCAAGAACAACC

Figure 2 – page 1

Sesame 11S Globulin 5'UTR Region (SEQ ID NO:2)

CAATAAGAAGTCCTCTCCTCTCCGAGCTAAATCCTTTGTATAAAAAAGTGCCTGTTCTTGTT
CATGATGGAAAGCCGCTGTCTGATTCCTCCATTATACTGGAGTACGTCGATCAGAAATGGAG
GTCCAACCCCTTGTTCCCGACGATCCCTACCAAAGAGCCCAAGCCCACTTATGGGCTAGAT
TTGCCGATGAGAAGGTACATGGGATAAAATACTTTTGCTTCTATATATATTTGATGACTAAT
AAAATTACGTGAATTCTTATTCGGTTTAGAAAATTTCATGCCGTAGAGATAATATGTGATCC
TAATCATACAATGTAATGACACCAGATAACTACTCTGAGCATATAAATTCCGTTGATCCTCA
GGTTCTTGAATCAGCATGGCTTGCTCTCTGTTCGGAAGGAAAGACGCAGGAGAGAGCAGTGA
AACAAGCCATTGAGAACCTGGAACATGTCGAAGAGAAGCTGAAAGGGAAGAGGTTCTTCGGA
GGGGACATAATTGGGCATGTGGACCTAATGATGGGCTTCGTTTCCTACATGTTGCCTGTTTG
GGAAGAGGTTGCCGGAGTGAAAATCCTGGATCCCCACAAATTCCCAGCTATAGCTGCCTGGA
CGAATAATTTCCTCAATCATGAAGCCATCAAGGCTGAATATTTGCCACCCACTGCTGAGACC
TTCACCTATTTCCAGTGGCGACGAAAAGAATTAATTCCTGTCTATGCCTCTTATGGACAGTA
GATGGTGTAaTCAACAAAAGTCGGAATAGAGAATCTGAGGCTGTATTAGAGGATAAATCGAA
GTCCAATTCATTGGACTGAGTACGAGGTTTTTAAGCGTTGTAATTTCTTGAAGCAGTACATC
TGCCTGTATTAGTACAGAGGATCCGTGCACCAAAAATCTTATCCACCCAAAAAGATCTCCTT
TTTATATAaATCTTGTACGCCCCGTCTTTCTTATTATAATTGTTCGTTTAGAATTTTCAGTA
TTTTTGGAAAGTATTTAGTATTGTTTGTTGTCAGTTTAAAATTTTCTTAGTTACTAAATTAT
TTTCAATATTTTACTTTAATTTGGTGTGTTTATATAATTTCATATTTATTTGAGATTTATGA
TCCATTATTATAATCATTTAATTATAAATATATGAAGTTTAATAAGTATTTAGCCCTTACGA
CTTACATATTCATATGGCTTTTTATAGTTAAATTTATCATGATTTTATAAGTTTTTATTAGG
CCACTTAACTTTTTGTAATTGCCAAATTCGTTACAACTACTTTGTCATTACCTTTTTACTTC
AGCACGTTGAGAAGGGAAGCCTTCGTATGATTTTTCAAAGTACTTCTTACATTTTTACTAGT
GTTTGAGAGTTTTGGCAaCGTGACTATGGATTGGTCATTGTCTCCTCATTCTCATGCCTAGA
GTCATAGCCAATCATTAATACACCAAGTAGGAAGTCAATCATAACCTTAAGAAAGTGACAAG
ACTTTATTCGAAATTAAATTATTAATATTTGAGCACAAACTATAAAAAATAAAATTTATTTT
TTGAGTAAAAGTATTAGATAATATTTTATTAAATAGTAAATTAATTTTAAAATTAAAATTA
TTTACACTCGAGATAAATTGCAGCAGCTATTAATTTTTTTTAAATTGAATTTTTATTATAA
AATTTTTACAAATATTTTAATAAACTTCGACCATAAATTATAAGAAATAAAAATTTAAAAAC
TAAAGAAATTATATTTTAATATAAATAAAAAATAGTTTATAACTTATAATTATATTTATTTT
TAGATAACTTCTAACATATTTTAATTATTTTAAAATTACAtattatttattctaaaaaaat
ttaataaactttgacaaagaaaagtaaaaataaaatttatttatttctacaatttatc
tacaatgtaaataattataatttaaaattatttaataaaaagtttatctaatacttttatt
caaaaataaattctacttttttatagtttgtgctcacatattaatatattttagaccaaata
ataatttaatttcaaaaatagtataatagatcctagaaattatctaaaaataaaataattat
aatttagaaccatttttattatatatattaaaatataattttttaatatttctatttttgt
aaaaataaaaattcttatagtttgtggccaaagttggtcaaaatatttttttttctttttaat
ggtacttaaaaaacacgtttcttttattttttggtaccttttaaataggtatttgaagttcaa
agtcatgttagtcaatagaagtttactaccgttaacggccacgtgcgggacacatggcctct
gttgttaacttgggacaaaaagtatgtttttgtgttttatagtaccaaaagtgacacttg
ccacaattatggtacccaaaataaaatcaactttttttaacggaatcaaaaaaaaaaaattt
tgcccttacataatatatgtactaatcaacggattgaattttctattgtaatattcatttca
ttttctatttcgttcaacatatacaattatgtatatttgaacgaaatcatatatttttatttt
gaaaaataaaaaaaaattaacacatgctatgtatatattgattgtaataaaaaataaaataa
ttaaaatttgcaacaaatgcaatccaaccaaacataatcgccacatacccattaggtgtaag

Figure 2 – page 2

```
cagagcagcatttccatacatgcaacctcatgatgatcataacaaaacaaaagcccatgcac
aatagataccgccaaatgtcgctcgtttctcaccatctcacactcgacgtgtcgacctcaac
ccaccaatttcaactataaatccccaccttctctattccccgcttcacatccatcatcagc
cccctcaaactactaatcccagcacctccaaac
```

NUCLEIC ACIDS FROM SESAME PLANTS

CROSS-REFERENCE TO RELATED APPLICATIONS

This is the U.S. National Stage of International Application No. PCT/US2004/024858, filed Jul. 29, 2004, which in turn claims the benefit of U.S. Provisional Application Ser. No. 60/490,873, filed Jul. 29, 2003, each of which is incorporated by reference in its entirety herein.

BACKGROUND

1. Technical Field

The invention relates to isolated nucleic acids that can be used to direct expression of a second nucleic acid operably linked thereto.

2. Background Information

Recombinant DNA technology has provided a new opportunity for engineering valuable traits in plants. Basically, foreign genes can be introduced into plants to alter metabolic pathways. Examples of products of plant metabolic engineering include herbicide tolerant plants, long-life tomatoes, improvement of seed nutritional quality, and production of novel compounds of industrial or pharmaceutical value. In some cases, engineering of new traits was made possible by the expression or suppression of a single gene while in other cases the expression or suppression of multiple genes during seed development was required.

Plant promoters that have been characterized to date include constitutive promoters such as promoters of actin and ubiquitin genes; promoters of genes involved in photosynthesis, such as the small subunit of ribulose 1,5-bisphosphate carboxylase and the chlorophyll a/b binding protein; root specific promoters identified upstream of mannopine synthase, putrescine N-methyltransferase, and hyoscyamine 6b-hydroxylase genes; promoters of patatin and sucrose synthase genes which direct specific expression in potato tuber; seed specific promoters of genes encoding lipoxygenase and lectin, oilseed rape napin, cruciferin, and oleosin, bean phaseolin and arcelin-5, oleate 12-hycroxyalse, rice amylase and glutelin, maize zein, and wheat puroindoline. Inducible promoters such as promoters of pathogenesis-related protein genes, promoters of heat shock proteins and herbicide inducible promoters of glutathione S-transferase. Artificial promoters like the regulation of maize CAB promoter with $E. coli$ lac repressor/operator system; the Tet repressor system; the induction system using animal steroid hormone receptors; copper controlled system using promoter elements of metallothionein gene; and fungal promoters induced by ethanol.

Seed storage proteins accumulate in discrete vesicles of protein bodies and constitute a major fraction of the proteins found in the mature seed. Seed storage proteins are used as sources of amino acids during germination and post-germinative growth of seedlings. Their corresponding mRNAs accumulate to high levels during the maturation phase and are mainly under transcriptional regulation. Seed storage proteins can be classified on the basis of their solubilities in various extraction solvents. The albumins are water-soluble, globulins are salt-soluble, prolamins are alcohol/water-soluble and glutelins are acid or alkali soluble. The globulins are further subdivided, based on their sedimentation coefficients, into two types, the 7S vicilin-type and the 11S legumin-type globulins.

Sesame (*Sesamum inidicum* L.) has been an important oil crop in Asian countries. Sesame seed contains approximately 50% oil and 19% protein. Approximately 70-85% of the oil is oleic and linoleic acids, which makes sesame a good source of edible oil. Sesame seed contains high levels of methionine, partly due to a sulfur-rich 2S albumin isoform, which contributes to its nutritional quality. Because of its flavor and nutrient content, sesame is directly consumed as an additive in food. The two major storage proteins in sesame are 11S globulin and 2S albumin, which constitute 80-90% of total seed protein. Recently, full-length cDNAs encoding 2S albumin, 11S globulin, and 7S globulin isoforms have been reported.

SUMMARY

The invention involves methods and materials related to gene expression. The present invention relates to the cloning and characterization of 5' untranslated regions directing the expression of 11S globulin and the 2S albumin coding sequences, specifically the cloning and sequencing of 5' untranslated regions (5'UTRs) from 2.4 kb 2S albumin and 2.95 kb 11S globulin genes from sesame. The tissue specificity and expression profiles of these promoters were analyzed using a GUS reporter gene.

In one aspect, the invention features an isolated nucleic acid having at least 30% sequence identity to SEQ ID NO:1, or at least 30% sequence identity to SEQ ID NO:2.

The isolated nucleic acid can have 75% or greater sequence identity to SEQ ID NO:1 (e.g., 85% or greater sequence identity to SEQ ID NO:1, 95% or greater sequence identity to SEQ ID NO:1, or 98% or greater sequence identity to SEQ ID NO:1), or can be SEQ ID NO:1. The isolated nucleic acid can have 75% or greater sequence identity to SEQ ID NO:2 (e.g., 85% or greater sequence identity to SEQ ID NO:2, 95% or greater sequence identity to SEQ ID NO:2, or 98% or greater sequence identity to SEQ ID NO:2), or can be SEQ ID NO:2.

In another aspect, the invention features a nucleic acid construct comprising an isolated nucleic acid having at least 30% sequence identity to SEQ ID NO: 1, or at least 30% sequence identity to SEQ ID NO: 2, operably linked to a heterologous nucleic acid. The construct can comprise a nucleic acid having 75% or greater sequence identity to SEQ ID NO:1, or can be SEQ ID NO:1. In some embodiments, the construct can comprise a nucleic acid having 75% or greater sequence identity to SEQ ID NO:2, or can be SEQ ID NO:2.

The isolated nucleic acids provided herein can be at least 50 nucleotides in length (e.g., at least 100 nucleotides in length, or at least 500 nucleotides in length).

The invention also features a transgenic plant cell containing such a nucleic acid construct, or a transgenic plant containing such a nucleic acid construct.

In another aspect, the invention features a method of making a transgenic plant cell. The method comprises introducing a nucleic acid construct as described herein into a plant cell; and selecting a plant cell that contains the nucleic acid construct. The invention also features a method of making a transgenic plant, comprising introducing a nucleic acid construct as described above into a plant.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control.

In addition, the materials, methods, and examples are illustrative only and not intended to be limiting.

Other features and advantages of the invention will be apparent from the following detailed description, and from the claims.

DESCRIPTION OF DRAWINGS

FIG. 1 is the sequence of a sesame 2S albumin 5'UTR (SEQ ID NO:1).

FIG. 2 is a sequence of a sesame 11S globulin 5'UTR (SEQ ID NO:2).

DETAILED DESCRIPTION

The invention provides methods and materials related to gene expression. The invention is based on the discovery of isolated nucleic acids that can be used to direct expression of another nucleic acid that is operably linked thereto. As used herein, the term "operably linked" refers to covalent linkage of a nucleic acid of the invention and a second nucleic acid in such a way as to permit or facilitate expression of the second nucleic acid. A nucleic acid of the invention can be incorporated into a nucleic acid construct. The resulting construct can be introduced into a cell or plant, and the second nucleic acid can be expressed in the cell or plant.

Nucleic Acids

As used herein, the term "nucleic acid" refers to RNA or DNA, including cDNA, synthetic DNA or genomic DNA. The term "isolated nucleic acid," as used herein, refers to a nucleic acid that is (i) free of sequences that normally flank one or both sides of the nucleic acid in a genome, (ii) incorporated into a vector or into the genomic DNA of an organism such that the resulting molecule is not identical to any naturally-occurring vector or genomic DNA, or (iii) a cDNA, a genomic nucleic acid fragment, a fragment produced by polymerase chain reaction (PCR) or a restriction fragment. In addition, an isolated nucleic acid can include an engineered nucleic acid such as a recombinant DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

A nucleic acid can be single- or double-stranded and can be coding or non-coding. Coding nucleic acids have nucleotide sequences that are transcribed into RNA molecules that can be translated to create polypeptides. Non-coding nucleic acids, typically, are transcribed into RNAs that cannot be translated. The term "expression" as used herein refers to the processes involved in producing a functional RNA molecule from a DNA molecule. The term a "functional RNA molecule" is meant to include an RNA molecule that is competent in performing its natural cellular role. An mRNA that acts as a template for synthesis of a functional polypeptide; a pre-mRNA that is processed into an mRNA; the RNA component of a ribosome that functions in protein translation; a catalytic RNA such as the catalytic component of ribonuclease P or the autocatalytic intervening sequence of pre-ribosomal RNA are some examples of functional RNA molecules. Processes involved in formation of a functional RNA molecule include, without limitation, proper initiation, elongation, and termination of transcription. Furthermore, proper processing of an RNA molecule, for example proper processing of a pre-mRNA molecule into an mRNA molecule from which a functional polypeptide can be translated, also is necessary for formation of a functional RNA molecule.

In some embodiments, a novel nucleic acid of the invention has 30% or greater sequence identity to SEQ ID NO: 1, for example, 35% or greater, 40% or greater, 50% or greater, 60% or greater, 70% or greater, 80% or greater, 85% or greater, 90% or greater, 95% or greater, 96% or greater, 97% or greater, 98% or greater, or 99% or greater. In some embodiments, an isolated nucleic acid of the invention has 30% or greater sequence identity to SEQ ID NO: 2, for example, 35% or greater, 40% or greater, 50% or greater, 60% or greater, 70% or greater, 80% or greater, 85% or greater, 90% or greater, 95% or greater, 96% or greater, 97% or greater, 98% or greater, or 99% or greater. The length of a nucleic acid is, for example, 50 to 100 nucleotides, 100 to 250 nucleotides, 250 to 500 nucleotides, 500 to 1,000 nucleotides, 1,000 to 2,000 nucleotides, or greater than 2,000 nucleotides.

As used herein, the term "sequence identity" refers to the degree of similarity between any given nucleic acid sequence and a target nucleic acid sequence. The degree of similarity is represented as percent sequence identity. Percent sequence identity is calculated by determining the number of matched positions in aligned nucleic acid sequences, dividing the number of matched positions by the total number of aligned nucleotides, and multiplying by 100. A matched position refers to a position in which identical nucleotides occur at the same position in aligned nucleic acid sequences. Percent sequence identity also can be determined for any amino acid sequence. To determine percent sequence identity, a target nucleic acid or amino acid sequence is compared to the identified nucleic acid or amino acid sequence using the BLAST 2 Sequences (Bl2seq) program from the stand-alone version of BLASTZ containing BLASTN version 2.0.14 and BLASTP version 2.0.14. This stand-alone version of BLASTZ can be obtained from Fish & Richardson's web site (World Wide Web at "fr" dot "com" slash "blast") or the U.S. government's National Center for Biotechnology Information web site (World Wide Web at "ncbi" dot "nlm" dot "nih" dot "gov"). Instructions explaining how to use the Bl2seq program can be found in the readme file accompanying BLASTZ.

Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to −1; -r is set to 2; and all other options are left at their default setting. The following command will generate an output file containing a comparison between two sequences: C:\Bl2seq-i c:\seq1.txt-j c:\seq2.txt-p blastn-o c:\output.txt-q −1-r 2. If the target sequence shares homology with any portion of the identified sequence, then the designated output file will present those regions of homology as aligned sequences. If the target sequence does not share homology with any portion of the identified sequence, then the designated output file will not present aligned sequences.

Once aligned, a length is determined by counting the number of consecutive nucleotides from the target sequence presented in alignment with sequence from the identified sequence starting with any matched position and ending with any other matched position. A matched position is any position where an identical nucleotide is presented in both the target and identified sequence. Gaps presented in the target sequence are not counted since gaps are not nucleotides. Likewise, gaps presented in the identified sequence are not counted since target sequence nucleotides are counted, not nucleotides from the identified sequence.

The percent identity over a particular length is determined by counting the number of matched positions over that length and dividing that number by the length followed by multiplying the resulting value by 100. For example, if (i) a 500-base nucleic acid target sequence is compared to a subject nucleic acid sequence, (ii) the Bl2seq program presents 200 bases from the target sequence aligned with a region of the subject sequence where the first and last bases of that 200-base region are matches, and (iii) the number of matches over those 200 aligned bases is 180, then the 500-base nucleic acid target sequence contains a length of 200 and a sequence identity over that length of 90% (i.e., 180, 200×100=90).

It will be appreciated that different regions within a single nucleic acid target sequence that aligns with an identified sequence can each have their own percent identity. It is noted that the percent identity value is rounded to the nearest tenth. For example, 78.11, 78.12, 78.13, and 78.14 are rounded down to 78.1, while 78.15, 78.16, 78.17, 78.18, and 78.19 are rounded up to 78.2. It also is noted that the length value will always be an integer.

Novel nucleic acids of the invention can be generated by methods such as site directed mutagenesis, splicing together of portions of different nucleic acids, de novo synthesis, deletion of nucleic acid segments from an existing nucleic acid, or insertion of nucleic acid segments into nucleic acids such as SEQ ID NOs. 1 and 2.

Expression Control Nucleic Acids

A novel nucleic acid of the invention typically contains one or more regulatory elements involved in initiating transcription. Such a nucleic acid is herein referred to as an expression control nucleic acid. The term "regulatory elements" refers to sequence motifs that modulate expression of a coding nucleic acid operably linked to the regulatory elements. Regulatory elements, for example, are recognized by DNA binding polypeptides such as RNA polymerase that catalyze transcription, or transcriptional repressors or transcriptional activators that, upon binding to their respective elements, will lead to a decrease or inhibition, or increase or induction, of expression from a second nucleic acid operably linked thereto.

Regulatory elements include, without limitation, -10 or -35 promoter elements on the DNA molecule where RNA polymerase binds to begin the process of transcription and cis-acting elements such as operators where repressors of gene expression bind and block transcription or enhancers where transcriptional enhancers (activators) bind and trigger binding of RNA polymerase for transcription. Regulatory elements also include response elements or inducible elements that modulate expression of a nucleic acid sequence.

Operator or enhancer elements in an expression control nucleic acid can be located (i) between the promoter elements and the transcriptional start point, (ii) upstream of the promoter elements, and/or (iii) at a location that is greater than 50, 100, 200, 400, or 800 nucleotides upstream of the transcription start point.

Regulatory elements can be the binding sites of general transcriptional activators/repressors or for more specialized transcriptional activators/repressors that regulate expression of coding sequences whose products function in particular developmental or environmental contexts. For example, an AT stretch (AT-1 box) is a binding site for a nuclear factor that acts as a general transcriptional activator. Examples of regulatory elements that are binding sites for specialized DNA-binding proteins include, without limitation, ABA-responsive elements which are recognized by abscissic acid (ABRE), a DNA binding protein that induces the transcription of specific sets of genes during seed maturation, and SEF4 binding motif, a regulatory element that is recognized by the DNA binding protein SEF, soybean embryo factor.

Regulatory elements involved in modulating expression of coding nucleic acids can be of variable lengths, for example as few as four nucleotides in length to greater than twenty nucleotides in length per repeat unit. Some examples of regulatory elements that are involved in modulating transcription include the eight nucleotide TGAAAAAT motif present upstream of B-hordein gene promoter of barley promoters of alpha-gliadin, gamma-gliadin, and low molecular weight glutenin genes of wheat, and the five-nucleotide CAACA-Binding consensus sequence of *Arabidopsis* transcription factor RAV1.

Regulatory elements that are involved in modulating transcription can be tissue or cell type specific. For example, promoter elements typically are most effective at mediating transcription predominantly in certain cell types, although cell type- or tissue specific promoters also may mediate expression in other cell types or tissues. Tissue- or cell type-specific promoters include, for example, those specific to vegetative tissues or those specific to reproductive tissues. Vegetative tissues, for example, include tissues such as ground meristem, vascular bundle, cambium, phloem, cortex, shoot apical meristem, lateral shoot meristem, root apical meristem, lateral root meristem, leaf primordium, leaf mesophyll, or leaf epidermis.

Methods for identifying and characterizing expression of regulatory elements in DNA include, for example, those described in the following references: Jordano et al. (1989) *Plant Cell* 1:855-866; Bustos et al. (1989) *Plant Cell* 1:839-854; Green et al. (1988) *EMBO J* 7: 4035-4044; Meier et al. (1991) *Plant Cell* 3: 309-316; and Zhang et al. (1996) *Plant Physiology* 110: 1069-1079.

Expression control nucleic acids often can be identified by function. For example, a putative expression control nucleic acid can be operably linked to a "reporter nucleic acid" or a "selectable marker nucleic acid". Examples of useful reporter nucleic acids are those that encode polypeptides such as β-galactosidase, β-glucuronidase (GUS), green fluorescence protein (GFP), luciferase, and chloramphenicol acetyltransferase (CAT). Useful selectable marker nucleic acids include antibiotic or herbicide resistance genes such as genes encoding resistance to ampicillin, neomycin, kanamycin, G418, bromoxynil, chloramphenicol, 2,4-dichlorophenoxyacetic acid, gentamicin, streptomycin, zeocin, blasticidin, chlorsulfuron, glyphosphate, bialofos, and phosphinothricin. Useful selectable marker nucleic acids also include those that encode enzymes involved in producing an essential substance. Examples include nucleic acids encoding phosphomannose isomerase, cytokinin glucuronides, mannose-6-phosphate isomerase, and xylose isomerase. See Reed et al. (2001) *In Vitro Cell Dev Biol—Plant* 37:127-132; and Joersbo (2001) *Physiologia Plantarum* 111:269-272. A reporter or selectable marker nucleic acid can be introduced into an expression vector (a nucleic acid vector containing an expression control nucleic acid of the invention). Alternatively, the reporter or selectable marker nucleic acid can be operably linked to an expression control nucleic acid of the invention both of which can be introduced into a nucleic acid vector. The resulting nucleic acid expression construct (a coding nucleic acid such as a reporter or selectable marker nucleic acid operably linked to an expression control nucleic acid inserted into a nucleic acid vector) can be introduced into a cell for expression. If expressed, the reporter encoded by the reporter nucleic acid or selectable marker can be detected by assaying for activity or by assaying for the presence of the encoded product.

Nucleic Acid Constructs

Expression control nucleic acids of the invention can be incorporated into nucleic acid constructs. A nucleic acid of interest can be operably linked to an expression control nucleic acid to generate nucleic acid expression constructs and in this way be expressed.

Heterologous nucleic acid molecules can encode polypeptides. As used herein, the term "heterologous nucleic acid" refers to a nucleic acid molecule other than an expression control nucleic acid of the invention and its naturally associated coding sequence, if any. As used herein, "polypeptide" refers to an amino acid polypeptide, regardless of length or post-translational modification. Polypeptides can include enzymes or fragments thereof that regulate growth, hormone production, photosynthetic efficiency, nutritional value, and oil or protein composition. Polypeptides can include reporter polypeptides such as β-glucuronidase and green fluorescent protein, and marker polypeptides such as neomycin phosphotransferase II. Polypeptides can include polypeptides such as those described in WO 9411516, WO 9311245, and in U.S. Pat. Nos. 6,124,524 and 6,307,1258. Polypeptides can provide, for example, resistance to environmental stresses such as drought and cold, pathogens, insects, or herbicides. Polypeptides that provide resistance to pathogens include those described in U.S. Patent Application Ser. No. 60/264, 776 and U.S. Pat. Nos. 5,993,808; 6,087,560; 6,066,491; and 6,087,161. Polypeptides that provide resistance to insects include those described in U.S. Pat. Nos. 5,380,831 and 6,218,188. Herbicide resistance to glyphosate and glufosinate can be provided by expressing nucleic acid molecules encoding 5-enolpyruvylshilimate-3-phosphate synthase (EPSPS) polypeptides and phosphinothricin acetyl transferase (PAT) polypeptides, respectively. See, for example, U.S. Pat. Nos. 4,940,835 and 5,489,520. In addition, resistance to glyphosate and glufosinate can be provided by expressing a nucleic acid molecule encoding the glpA and glpB genes from *Pseudomonas* in the plastid of plants. See, for example, WO 99/05265. Resistance to imidazoline type herbicides can be provided by expression of a nucleic acid molecule encoding an acetohydroxyacid synthase polypeptide. See, for example, U.S. Pat. No. 4,761,373. Resistance to cyclohexanedione or aryloxyphenoxypropanoic acid type herbicides can be provided in corn by expression of nucleic acid molecules encoding herbicide resistant acetyl CoA carboxylase polypeptides (ACC1 and ACC2). See, for example, WO 98/08963 and Herbert et al. (1997) *Pestic Sci* 50:67-71. Expression of a protoporphyrinogen oxidase polypeptide resistant to porphyrric herbicides provides herbicide resistance to protoporphyrinogen inhibiting herbicides. See, for example, WO 98/29554. Resistance to benzyoylcyclohexanedione type herbicides can be provided by expression of a nucleic acid molecule encoding herbicide resistant 4-hydroxyphenylpyruvate dioxygenase polypeptides. See, for example, Barta and Boger (1996) *Pestic Sci* 48: 109-116; WO 98/02562; and WO 99/24586. Herbicide resistance also can be provided by expression of nucleic acid molecules encoding single chain Fv antibodies that bind herbicide. Expression of single chain Fv antibodies having specific binding affinity for viral coat proteins in, for example, the cytosol of plants, can provide resistance to viral pathogens. See, for example, Conrad and Fiedler (1998) *Plant Mol Biol* 38: 101-109 and WO 98/42852.

Heterologous nucleic acid molecules also can encode polypeptides such as those described in U.S. Pat. Nos. 6,211,440; 6,180,850; 6,171,864; 6,127,603; 6,111,167; 6,265,639; 6,235,514; 6,194,185; 6,043,072; 6,008,043; 5,871,998; 5,891,697; and 6,054,636.

Heterologous nucleic acid molecules also can be transcribed into ribozymes that cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contain a 5'-UG-3' nucleotide sequence. The construction and production of hammerhead ribozymes is known in the art. See, for example, U.S. Pat. No. 5,254,678. Hammerhead ribozyme sequences can be embedded in a stable RNA such as a transfer RNA (tRNA) to increase cleavage efficiency in vivo. RNA endoribonucleases such as the one that occurs naturally in *Tetrahymena thermophila* also are useful. See, for example, U.S. Pat. No. 4,987,071.

Heterologous nucleic acids can include complete coding sequences or less than full-length coding sequences and can be linked to an expression control nucleic acids of the invention in a sense or antisense orientation to generate full-length or less than full-length antisense or sense RNA molecules.

Constructs comprising a heterologous nucleic acid operably linked in sense orientation to an expression control nucleic acid of the invention can be used to inhibit the expression of an endogenous gene. In this instance, the heterologous nucleic acid has a nucleic acid sequence corresponding to all or part of the endogenous gene. Co-suppression using full-length cDNA sequences as well as partial cDNA sequences is known. See, e.g., U.S. Pat. Nos. 5,034,323 and 5,231,020 for a description of co-suppression technology. See also, WO99/15682.

Antisense RNA has been used to inhibit plant target genes using an entire cDNA sequence as well as a partial cDNA sequence. There is also evidence that 3' non-coding sequence fragments and 5' coding sequence fragments can play important roles in antisense inhibition. Antisense nucleic acid constructs include a nucleic acid molecule of interest that is operably linked, in antisense orientation, to the expression control nucleic acid of the invention.

In another alternative, the heterologous nucleic acid can include a sequence that is transcribed into an interfering RNA (RNAi). RNAi technology utilizes constructs that produce aberrant RNA transcripts, which disrupt transcription and/or translation of a corresponding endogenous nucleic acid. See, for example, U.S. Pat. No. 6,506,559; WO 99/53050; WO 01/12824; and WO 01/29058 for a description of RNAi technology and its use in decreasing expression of an endogenous nucleic acid. Such an RNA can be one that can anneal to itself, e.g., a double stranded RNA having a stem-loop structure. One strand of the stem portion of a double stranded RNA comprises a sequence that is similar or identical to the sense coding sequence of an endogenous nucleic acid, and that is from about 10 nucleotides to about 2,500 nucleotides in length. The length of the sequence that is similar or identical to the sense coding sequence can be from 10 nucleotides to 500 nucleotides, from 15 nucleotides to 300 nucleotides, from 20 nucleotides to 100 nucleotides, or from 25 nucleotides to 100 nucleotides. The other strand of the stem portion of a double stranded RNA comprises an antisense sequence of an endogenous nucleic acid, and can have a length that is shorter, the same as, or longer than the corresponding length of the sense sequence. The loop portion of a double stranded RNA can be from 10 nucleotides to 5,000 nucleotides, e.g., from 15 nucleotides to 1,000 nucleotides, from 20 nucleotides to 500 nucleotides, or from 25 nucleotides to 200 nucleotides. The loop portion of the RNA can include an intron.

Nucleic acid vectors suitable for use in creating a nucleic acid construct are commercially available and used routinely by those of ordinary skill. A nucleic acid vector can be a prokaryotic or eukaryotic vector. For example, a nucleic acid vector can be a plant vector, a bacterial vector, or one that can replicate in both a plant and a bacterial cell. The choice of nucleic acid vector can be determined based on cell or tissue specificity, efficiency of replication in a cell or tissue of interest, or type of selectable marker present.

Transgenic Cells and Transgenic Plants

An expression construct, e.g., a nucleic acid vector containing a heterologous coding nucleic acid operably linked to an expression control nucleic acid can be introduced into a host cell to generate a transgenic cell or organism. The level of gene expression or suppression in transgenic cells and organisms is influenced by the strength and the tissue specificity of the expression control nucleic acid that is operably linked to it. The most widely used promoter for the transcription of foreign genes in plants is the promoter for cauliflower mosaic virus 35S RNA. However, the use of the same promoter to direct the expression of multiple genes may damage the plant due to undesirable accumulation of high levels of foreign proteins and metabolites. Also, the presence of multiple copies of the same promoter in a genome can cause gene silencing. Therefore, the use of a plurality of genes in transgenic cells and organisms is facilitated by the use of a different promoter with suitable function and regulation for each gene. The expression control nucleic acids described herein fulfill such a need.

The term "host" or "host cell" includes not only prokaryotes such as *E. coli*, but also eukaryotes such as plant cells. Plant cells include, for example, cells from alfalfa, canola, sunflower, and soybean. Nucleic acid expression constructs can be introduced into a host cell by various known methods, for example, transformation or transfection, electroporation, lipofection, and particle bombardment. Host cells containing a nucleic acid expression construct of the present invention may be used for such purposes as propagating the expression construct, producing a nucleic acid (e.g., an interfering RNA) or expressing a polypeptide.

An expression construct containing a heterologous coding nucleic acid operably linked to an expression control nucleic acid can be used to generate a transgenic plant. Techniques for introducing exogenous nucleic acids into monocotyledonous and dicotyledonous plants are known in the art, and include, without limitation, *Agrobacterium*-mediated transformation, viral vector-mediated transformation, electroporation, and particle gun transformation. Techniques for introducing nucleic acids into plants are described in U.S. Pat. Nos. 5,204,253; 6,013,863; and 6,051,756. If a cell or tissue culture is used as the recipient tissue for transformation, plants can be regenerated from transformed cultures by techniques known to those skilled in the art.

Transgenic plants may be entered into a breeding program, e.g., to introduce a nucleic acid encoding a polypeptide into other lines, to transfer the nucleic acid to other species or for further selection of other desirable traits. Alternatively, transgenic plants may be propagated vegetatively for those species amenable to such techniques. Progeny includes descendants of a particular plant or plant line. Progeny of an instant plant include seeds formed on $F_1$, $F_2$, $F_3$, $F_4$ and subsequent generation plants, or seeds formed on $BC_1$, $BC_2$, $BC_3$, and subsequent generation plants. Seeds produced by a transgenic plant can be grown and then selfed (or outcrossed and selfed) to obtain seeds homozygous for the nucleic acid encoding a novel polypeptide.

Hybrid varieties can be produced by preventing self-pollination of female parent plants (i.e., seed parents), permitting pollen from male parent plants to fertilize female parent plants, and allowing $F_1$ hybrid seeds to form on the female plants. Self-pollination of female plants can be prevented by emasculating the flowers at an early stage of flower development. Alternatively, pollen formation can be prevented on the female parent plants using a form of male sterility. For example, male sterility can be cytoplasmic male sterility (CMS), nuclear male sterility, genetic male sterility, molecular male sterility wherein a transgene inhibits microsporogenesis and/or pollen formation, or be produced by self-incompatability. Female parent plants containing CMS are particularly useful. Useful CMS for *Brassica* species can be, for example of the ogu (Ogura), nap, pol, tour, or mur type. In embodiments in which the female parent plants are CMS, the male parent plants typically contain a fertility restorer gene to ensure that the $F_1$ hybrids are fertile. See, e.g., U.S. Pat. Nos. 5,644,066, 6,229,072 and 6,392,127.

The methods of the invention can be used to form single-cross $F_1$ hybrids. In such embodiments, the parent plants can be grown as substantially homogeneous adjoining populations to facilitate natural cross-pollination from the male parent plants to the female parent plants. The $F_1$ seed formed on the female parent plants is selectively harvested by conventional means. One also can grow the two parent plants in bulk and harvest a blend of $F_1$ hybrid seed formed on the female parent and seed formed upon the male parent as the result of self-pollination. Alternatively, three-way crosses can be carried out wherein a single-cross $F_1$ hybrid is used as a female parent and is crossed with a different male parent that satisfies the fatty acid parameters for the female parent of the first cross. As another alternative, double-cross hybrids can be created wherein the $F_1$ progeny of two different single-crosses are themselves crossed. Self-incompatibility can be used to particular advantage to prevent self-pollination of female parents when forming a double-cross hybrid.

Hybrids typically have good agronomic properties and exhibit hybrid vigor, which results in seed yields that exceed that of either parent used in the formation of the $F_1$ hybrid. For example, yield can be at least 10% (e.g., 10 to 20%, 10 to 15%, 15 to 20%, or 25 to 35%) above that of either parent. Yield can be at least 10% (e.g., 10 to 15% or 15 to 20%) above that of an open-pollinated variety.

A suitable group of plants with which to practice the invention include dicots, such as safflower, alfalfa, soybean, rapeseed (high erucic acid and canola), or sunflower. Dicotyledonous plants include plants of the following genera: *Arachis, Atropa, Beta, Brassica, Capsicum, Carthamus, Citrullus, Citius, Cocos, Coffea, Cucumis Cucurbita, Daucus, Fragaria, Glycine, Gossypium, Helianthus, Lactuca, Lupinus, Lycopersicon, Malus, Manihot, Medicago, Nicotiana, Olea, Phaseolus, Pisum, Prunus, Raphanus, Ricinus, Sesamum, Sinapis, Solanum, Sorghum, Theobromus, Vicia* and *Vitis*.

Particularly useful are *Brassica* species such as *B. napus, B. rapa, B. nigra* and *B. juncea*. Transgenic open-pollinated or hybrid *Brassica* plants are useful for producing a harvested crop that can be used to make a crude canola oil or a refined, bleach, and deodorized canola oil. For example, $F_1$ hybrid seed harvested from female plants can be planted and $F_2$ seed harvested from the resulting plants. Harvested canola seed can be crushed by techniques known in the art.

In some embodiments, plants are vegetable crops or root crops such as potato, broccoli, peas, sweet corn, popcorn, tomato, beans (including kidney beans, lima beans, dry beans, green beans) and the like.

Other Uses

In some embodiments, a nucleic acid can be used as a probe or primer. Such a nucleic acid can be at least 40 nucleotides in length, but less than the full length of an expression control nucleic acid of the invention. Probes can be obtained by standard methods. For example, restriction enzyme digestion of expression control nucleic acids of the invention can be used to generate nucleic acid probes of various lengths, for example, greater than 1,000 nucleotides, 1,000 nucleotides, 500 nucleotides, 250 nucleotides, 100 nucleotides, 50 nucleotides, or less than 50 nucleotides. Alternatively, nucleic acid probes can be synthesized by standard nucleic acid synthesis techniques. Nucleic acid probes can be used in standard nucleic acid hybridization methods such as for example, Southern hybridization, Northern hybridization, and colony hybridization. Probes can be also be used in molecular breeding techniques.

Nucleic acids of the invention also can be incorporated into nucleic acid constructs that may be used in techniques such as chimeraplasty to alter an endogenous nucleic acid sequence of an organism. See for example U.S. Pat. No. 6,297,056.

The invention will be further described in the following examples, which do not limit the scope of the invention described in the claims.

EXAMPLES

Example 1

Materials and Methods

Antibody production: Seeds were collected from sesame plants during seed development at 10, 20, 30, and 40 days after flowering. Storage proteins were extracted from the seeds with water, followed by extraction with 1 M NaCl. Salt soluble proteins were resolved in SDS-PAGE gel and detected by staining with Coomassie blue. Stained bands (5 major bands between 21 to 31 kda) were cut from 8 different gels and antibodies were made against each protein band by Cocalico Biologicals. Antibodies were evaluated via Western blot analysis against sesame and *Brassica* proteins from leaves and seeds. Out of 10 antibodies (2 antibodies/protein band) tested, three were specific to sesame seed proteins.

Library preparation and screening: Total RNA was isolated from sesame seeds collected from plants at 20 to 30 days after flowering, and used to construct a PCR based expression cDNA library using the SMART™ cDNA library kit from Clontech. The expression library was screened with the antibodies described above. Two positive clones were identified and their nucleotide sequences were determined. The two clones had nucleotide sequences identical to 2S albumin and 7S globulin storage proteins from sesame.

Promoter Capture: The 5'UTR regions of sesame 2S albumin and 11S globulin genes were cloned and sequenced using a genome walking procedure. In general, the procedure involves digesting genomic DNA with a series of restriction enzymes known to digest within the gene of interest. Then an adaptor is ligated to the ends of the DNA fragments. With adaptor and gene specific primers, a series of PCR amplifications are done to produce the sequence of interest. This fragment is then sub-cloned into a TA vector for analysis.

Gene specific primers were designed based on the 2S albumin coding sequence described above, and on the published coding sequences of 11S globulin storage proteins. The gene-specific primers and a Universal Genome Walker™ kit (Clontech) were used to capture 5'UTR fragments. Genome walking captured fragments upstream of the 2S albumin and 11S globulin coding sequences of about 600 and 750 bp, respectively. Captured fragments were cloned and sequenced. New specific primers were designed based on the captured fragments and used for a second round of genome walking. The second walk yielded an additional fragment of about 1.78 kb in length upstream of the 2S albumin coding sequence and an additional fragment of about 2.2 kb in length upstream of the 11S globulin coding sequence. Therefore, the length of 5'UTR captured from the 2S albumin gene was about 2.4 kb (0.6+1.78) and the length of 5'UTR captured from the 11S globulin gene was about 2.95 kb (0.75+2.2).

The DNA fragments captured from the second genome walk were cloned and sequenced. The 2S albumin 5'UTR fragment was amplified using the forward primer "2sAlb-proF" (GTCGACCTGAAATCATGTGAACTCAT-AAAATG) (SEQ ID NO: 3) and the reverse primer "2sAlb-proR" (GGATCCGGTTGTTCTTGAACTGAGATTTATATG) (SEQ ID NO: 4). The 5' ends of these primers were engineered to include a SalI site in the forward primer and a BamHI site in the reverse primer. The 11S globulin 5'UTR fragment was amplified using the forward primer "11sGlob-proF" (AAGCTTCAATAAGAAGTCCTCTCCTCTCC) (SEQ ID NO: 5),and the reverse primer "11sGlobproR" (CTAGAGTTTGGAGGTGCTGGGATTAGTAG) (SEQ ID NO: 6). The 5' ends of these primers were engineered to include a HindIII site in the forward primer and an XbaI site in the reverse primer. SEQ ID NO:1 sets forth the nucleotide sequence of the 2S albumin 5'UTR fragment. SEQ ID NO:2 sets forth a nucleotide sequence of the 11S globulin 5'UTR fragment.

Constructs: The 2.4 kb 5'UTR DNA fragment of 2S albumin, generated by PCR amplification (see "promoter capture") was cloned into the TA vector pCR2.1 to generate a construct designated pMB345. Cloning of the 2.95 kb 5'UTR DNA fragment of 11S globulin into the TA vector pCR2.1 resulted in the recovery of a construct having a sub-fragment of about 1.11 kb in length. This construct was designated pMB349. The 11S globulin sub-fragment in pMB349 corresponds to the portion of the 11S globulin 5'UTR that is immediately 5' to the 11S globulin coding region. The nucleotide sequence of the 1.11 kb sub-fragment is marked in lower case letters in SEQ ID NO:2.

The 2S albumin and 11S globulin 5'UTR fragments set forth in SEQ ID Nos.: 1 and 2, respectively, were each operably linked to a GUS reporter gene to create a GUS-NOS/pSP72 construct. The GUS-NOS/pSP72 construct, designated pMB160, was generated by cutting GUS-NOS cassette from pBI121.1 (Clontech) with XbaI/EcoRI and subcloning in the pSP72 vector at the XbaI/EcoRI sites. pMB345 was digested with BamHI/SalI and the 2S albumin promoter DNA fragment was subcloned at the BamHI/XhoI sites in GUS-NOS/pSP72 to generate a construct designated pMB352.

pMB349 was digested with HindIII/XbaI, and the 11S globulin promoter DNA fragment was subcloned at the HindIII/XbaI sites in GUS-NOS/pSP72 to generate a construct designated pMB348. Orientation and cloning was verified via sequencing and restriction mapping.

The pMB354 construct was created by sub-cloning the pMB352 NaeI/EcoRI fragment, which includes the sesame 2S albumin 5' UTR/GUS/NOS terminator cassette, into pMOG800 at the SmaI/EcoRI sites. The pMB351 construct was created by sub-cloning the pMB348 HindIII/EcoRI fragment, which includes the 11S globulin 5' UTR/GUS/NOS terminator cassette into pMOG800 at the HindIII/EcoRI sites.

Example 2

2S Albumin and 11S Globulin Sequence Analysis

Sequence analysis indicated that both 5'UTR fragments contain inverted repeats and dyad repeats. The 11S globulin 5'UTR appears to have more repeats than does the 2S albumin 5'UTR. The 11S globulin 5'UTR also contains direct repeats.

When subjected to BLAST analysis against a GeneBank database, some plant and non-plant genomic regions of 20 to 37 base pairs in length were found to have sequence similarity to regions in the 2S albumin and 11S globulin 5'UTR fragments. For example the 2S albumin 5'UTR fragment sequence at position 227 to 263, tcagaaatctcgtgtggaaagtgccgctcatcgcacc, exhibits 94% sequence identity with a *Medicago trancatula* sequence at position 98297-98261, tcagaaatctcgtgtggaaagtgccgctcatcgcacc. Compare Table 1 and BAC clone mth2-18j5, Accession No. AC126014.

The 2S albumin and 11S globulin 5'UTR fragments were analyzed using computer software analysis programs from DNAStar (GeneQuest) and "Place." The two 5'UTR fragments have 24% overall nucleotide sequence identity, using the DNAStar GeneQuest software program and default parameters. Several regulatory elements were identified in both fragments. See Tables 1 and 2. Regulatory elements include:

1. E-box element (CANNTG): confers seed specific expression (Kawagoe et al. (1994) *Plant J* 5:927-936.)
2. CAAT-box: Helps define RNA polymerase binding site. Enhances transcription (Shirsat et al. (1989) *Mol Gen Genet* 215:326-331)
3. TATA-box: Positions RNA polymerase II for transcription initiation (Shirsat et al. (1989) *Mol Gen Genet* 215: 326-331)
4. TGAC motif: Confers seed-specific gene expression (De Pater et al. (1993) *Plant Cell.* 5 :877-886)
5. Transcription initiation sequence CTCATCAA described by Joshi (1987) *Nucl Acids Res* 15: 6643-6653.
6. SEF4 binding motif: Soybean embryo factor (SEF) is a nuclear DNA binding protein. Expression of SEF begins in mid-maturation of soybean embryo and increases moderately during embryo development. SEF4 is reported to activate expression of the β-subunit of β-conglycinin. (See Lessard et al. (1991) *Plant Mol Biol* 16:397-413.)
7. ABRE: ABA-responsive elements (ABRE) are a subset of the G-box family of cis-acting elements (see Guiltinan et al. (1990) *Science* 250: 267-271; Mundy et al. (1990) *Proc Natl Acad Sci USA* 87: 1406-1410; Williams et al. (1992) *Plant Cell* 4: 485-496). The ABRE consensus sequence "ACGTGG" is conserved in a variety of abscissic acid-regulated genes. ABRE are bound in a sequence-specific manner by a nuclear DNA-binding protein containing a leucine zipper structure. (See Guiltinan et al. (1990) *Science* 250: 267-271.)
8. AT-1 box: An AT-rich element. Binding site for a nuclear factor that acts as a general transcription activator (Bustos et al. (1989) *Plant Cell* 1: 839-853; Datta and Cashmore (1989) *Plant Cell* 1:1069-1077.
9. RY motif "CATGCATG," described by Dickinson et al. (1988) *Nucl Acids Res* 16: 371, directs seed specific transcription.
10. GCCATTG motif found in an oleosin promoter region described by Keddie et al. (1994) *Plant Molecular Biology.* 24: 321-340).
11. CCACC motif: present in multiple copies upstream of a number of genes encoding seed storage proteins from legumes (see Thomas et al. (1993) *Plant Cell* 5: 1401-1410).
12. AACACA motif confer seed specific expression (Goldberg (1986) *Phil Trans R Soc Lond* 314: 343-353).
13. CAAACAC element is conserved in many storage-protein gene promoters. May be responsible for the high activity of the napA promoters (Stalberg et al. (1996) *Planta* 199:515-519).
14. (CA)n element core (CNAACAC) found in *B. napus* storage protein genes. Needed for endosperm and embryo specific expression. (Ellerstrom et al. (1996) *Plant Mol Biol* 32:1019-1027).
15. ACACNNG element may be involved in seed specific and/or ABA induced expression. Also, this element can interact with a novel class of bZIP transcription factors (Kim et al. (1997) *Plant J* 11: 1237-1251).
16. GATA-box: A type IV zinc finger protein-binding motif. May be involved with light regulated gene expression (Teakle et al. (2002) *Plant Mol Biol.* 50:43-57).
17. CAACA element: AP2-like binding consensus sequence of *Arabidopsis* transcription factor RAV1 (Kagaya et al. (1999) *Nucleic Acids Res* 27: 470-478).
18. –300 motif (TG). One of two conserved regions of the –300 element, also known as the prolamin box or endosperm element. Present upstream of some storage protein promoters of barley and wheat. It is contained in a region necessary for endosperm-specific expression in low molecular weight glutenin. Involved in nitrogen response. (Thomas and Flavell (1990) *Plant Cell* 2:1171-1180; Müller and Knudsen (1993) *The Plant Journal* 4, 343-355).
19. Soybean embryo factor 1 (SEF1) binding motif (ATATTTATT) found upstream to soybean β-conglicinin (7S globulin) gene (Lessard et al. (1991) *Plant Mol Biol* 16:397-413).
20. GA responsive elements (GARE) (TAACAAA, TATCCAC): Central elements of gibberellin (GA) response complex (GARC) in high-pI alpha-amylase gene in barley. Similar to c-myb and v-myb consensus binding site (Gubler et al. (1995) *Plant Cell* 7:1879-1891; Gubler et al. (1992) *Plant Cell* 4:1435-41).
21. Pyrimidine box (CCTTTT). Part of the Gibberelline responsive complex (GARC). BPBF transcription factor binding site. (Mena et al. (2002) *Plant Physiol* 130:111-9).
22. AAAG—Core sequence required for the binding of Dof (DNA-Binding with One Finger) proteins in maize. This family of plant proteins may be involved in signal responsive and/or tissue specific expression (Yanagisawa and Schmidt (1999) *J Biol Chem* 267:23515-23519).
23. AATCCAAC-ribulose-1,5-bisphosphate carboxylase general consensus sequence AATCCAA or AATCCAAC (Manzara and Gruissem (1988) *Photosynth Res* 16:117-139).

24. S1F box (ATGGTA): Conserved in many plastid related genes. May act as a negative transcription factor (Zhou et al. (1992) *J Biol Chem* 267:23515-23519).
25. Box A element (CCGTCC): One of three common cis-acting elements found in phenylalanine ammonia-lyase (PAL) genes (Logemann et al. (1995) *Proc Natl Acad Sci* 92:5905-5909).
26. Auxin response element (TGTCTC): Arabidopsis ARF1 (auxin response factor) binding site (Ulmasov et al. (1997) *Science* 276:1865-1868).
27. Ethylene responsive element (AWTTCAAA): Possible binding site involved in transcriptional activation (Itzhaki et al. (1994) *Proc Natl Acad Sci USA* 91:8925-8929).

TABLE 1

Elements in Sesame 2S Albumin 5'UTR

| Motif | Sequence | Position in SEQ ID NO: 1 |
| --- | --- | --- |
| TGAC | TGAC | 2026–2029, 410–413, 434–437, 530–533, 985–988, 1346–349, 1484–1487 |
| CAAT-Box | CAAT | 1849–1852, 2035–2038, 2269–2272, 398–401, 629–632, 1017–1020, 1147–1150, 1166–1169, 1388–1391, 1586–1589 |
| RY-like motif "CATGCATG" | N(T/C/A)TGCANN | 1048–1055; 293–300; 1309–1316; 759–766; 1013–1020; 1032–1039; 1872–1879; 1917–1924; 1811–1818; 2187–2194; 2287–2294 |
| TATA box | TATAAT | 414–420, 2308–2314, 2376–2376 |
| CANNTG | CANNTG | 430–435, 591–596, 677–682, 1401–1406, 1457–1462, 1531–1536, 1567–1572, 2185–2190, 8–13, 60–65, 160–165, 406–165 |
| Unknown | TCAGAAATCTCGT GTGGAAAGTGCCG CTCATCGCACC (SEQ ID NO: 7) | 227–263 |
| CCACC | CCACC | 262–266, 2252–2256, 2331–2335 |
| ABRE consensus sequence | ACGTGG | 161–166 |
| CTCATCTA | CTCATCTA | 2355–2362 |
| SEF4 motif | CATTTTA CATTTTG | 763–769; 2102–2108 |
| GCCATTG | GCCATTG | 1536–1542 |
| AT stretch | TAATATTAATTA (SEQ ID NO: 8) | 2121–2132 |
| CAAACAC | CAAACAC | 1160–1166 |
| AACACA | AACACA | 382–387, 2262–1167 |
| GATA Box | GATA | 54–57, 389–392, 693–696, 914–917, 1180–1183, 1223–1226, 1232–1235, 1297–1300, 1325–1328, 1617–1620, 1767–1770, 1870–1873, 2009–2012 |
| CAACA | CAACA | 381–385, 1313–1317, 2182–2186, 2273–2277 |
| SEF1(ATATTTAWW) | ATATTTATT | 1103–1111 |
| GARE (Giberillin responsive element) | TAACAAA | 2768–2774 |
| Pyrimidine Box | CCTTTT | 1487–1492 |
| Box A | CCGTCC | 2248–2253 |
| Auxin response element | TGTCTC | 1996–2001 |
| Ethylene responsive element (ERE) | AWTTCAAA(A) | 1850–1857 |
| (CA)n element | CNAACAC | 1160–1166 |

TABLE 2

Elements in Sesame 11S Globulin 5'UTR

| Motif | Sequence | Position in SEQ ID NO: 2 |
| --- | --- | --- |
| TGAC | TGAC | 241–2444, 327–330, 1385–1388, 1482–1485, 1872–1875, 2410–2413 |
| CAAT-Box | CAAT | 2857–28560, 2790–2793, 2686–2689, 2566–2569, 2422–2425, 2307–2310, 1925–1928, 1914–1917, 1462–1465 |
| RY-like motif "CATGCATG" | (C/T/A)ATGC(A/C/T)(A/C/T) | 2747–2754; 2784–2791; 2784–2790; 285–292; 1417–1424; 725–732; 2627–2634; 2682–2689; |

TABLE 2-continued

Elements in Sesame 11S Globulin 5'UTR

| Motif | Sequence | Position in SEQ ID NO: 2 |
| --- | --- | --- |
| TATA box | TATAAT | 2867–2873 |
| CANNTG | CANNTG | 512–517, 865–870, 1189–1194, 2334–2339, 2345–2350, 2413–2418, 2625–2630, 2680–2685, 2803–2808 |
| CCACC | CCACC | 665–569, 911–915, 2853–2857, 2876–2880 |
| CTCATCTA-like element | (A/T/C)(A/T/C)CATC(A/C/T)N | 2906–2913; 2903–2910; 2899–2906; 2822–2829 |
| SEF4 binding motif | CATTTT(T/A/C) | 1352–1357, 2120–2125, 2541–2546 |
| GCCATTG | GCCATTG | 440–446 |
| AT1 Box | AATATTTTATT (SEQ ID NO: 9) | 1570–1581 |
| AACACA | AACACA | 2623–2628 |
| ACACNNG | ACACNNG | 329–335, 1616–1622, 2344–2350, 2412–2418, 2624–2630, 2830–2836 |
| GATA Box | GATA | 209–212, 296–299, 335–338, 796–799, 1567–1570, 1624–1627, 2795–2798 |
| CAACA | CAACA | 756–760, 2557–2561, 2677–2681 |
| -300 Element 'TGHAAARK' | TGAAAAAT | 2604–2611 |
| SEF1 'ATATTTAWW' | ATATTTATT | 1096–1104, 1788–96 |
| TAACAAA | TAACAAA | 2768–2774 |
| AATCCAA | AATCCAA | 2687–94 |
| S1F box | ATGGTA | 2231–2236, 2427–2432 |
| AAAG | AAAG | 45–48, 71–74, 157–160, 412–415, 476–479, 707–710, 761–764, 919–922, 1000–1003, 1339–1342, 1478–1481, 1558–1561, 1738–1741, 1876–1879, 1882–1885, 1962–1965, 2200–2203, 2293–2296, 2376–2379, 2406–2409, 2778–2781 |
| Pyrimidine Box | CCTTTT | 927–932, 1291–1296 |

Example 3

Functional Analysis of Expression Control Nucleic Acids

The transient expression functionality of the 2S albumin and the 11S globulin 5'UTR fragments was evaluated in *Brassica* leaves, embryos, and protoplasts using the pMB348 and pMB352 constructs. The results are shown in Table 3. Controls included the promoterless GUS-NOS/pSP72 construct pMB160, and the 35S-GUS-NOS/pSP72-construct pIMC38. The pMB160 construct did not show any significant leaky expression of GUS in either embryo or leaf tissue. High levels of GUS expression were observed in *Brassica* embryos when constructs having the 2S albumin or the 11S globulin 5'UTR fragments were used. Levels of GUS expression in leaf tissue using the 2S albumin or the 11S globulin 5'UTR fragment constructs were similar to those observed with the pMB160 construct. The 35S promoter construct (pIMC38) directed high levels of GUS expression in the leaf, embryo, and protoplasts. Levels of GUS expression in protoplasts using the 2S albumin or the 11S globulin 5'UTR fragment constructs were less than the levels obtained with the pIMC38 construct. The data suggest that the sesame 2S albumin and 11S globulin 5'UTR fragments direct transient expression preferentially in *Brassica* embryo tissue relative to *Brassica* leaf and protoplast tissues.

TABLE 3

Functional Analysis of 5'UTR Fragments

| | | | Tissues Used For Transient Expression | | |
| --- | --- | --- | --- | --- | --- |
| Constructs | Construct Description | Method of DNA Delivery | Embryos (Embryos with GUS activity/Total Embryos) | Leaves [Blue Dots (GUS activity)/Leaf] | Protoplasts (Protoplasts with GUS activity/3 cm Petri dish of protoplasts) |
| pMB160 | GUS-NOS-pSP72 | Biolistics | (2/99) | 1 | 4 |
| pIMC38 | 35S-GUS-NOS-pSP72 | Biolistics | (84/98) | 1000 | 600–700 |
| pMB348 | Glob(p)-GUS-NOS-pSP72 | Biolistics | (89/99) | 3 | 50–60 |
| pMB352 | Alb(p)-GUS-NOS-pSP72 | Biolistics | (121/131) | 2 | 11 |

Example 4

Further Functional Analysis of Expression Control Nucleic Acids

The functionality of the 2S albumin and the 11S globulin 5'UTR fragments was further evaluated in transgenic *Brassica* plants. The binary constructs pMB354 and pMB351 carrying the sesame 2S albumin and 11S globulin 5'UTR fragment operably linked to a GUS coding sequence, respectively, were introduced into Brassica cells in tissue culture by *Agrobacterium*-mediated transformation using a kanamycin selectable marker gene. The results are shown in Table 4.

Tissues of regenerated $T_1$ plants transformed with the pMB351 construct did not exhibit GUS activity. From about 20 days after flowering, $T_2$ seeds of 35 $T_1$ plants carrying the pMB351 construct stained strongly for GUS activity. $T_4$ seeds of 13 out of 20 $T_3$ plants carrying the pMB351 construct also stained strongly for GUS activity. $T_3$ microspores from 7 $T_2$ transgenic plants of the same line carrying the pMB351 construct were isolated and cultured essentially according to Chen et al. (Plant Breed. 113: 217-221, 1994). $T_3$ microspores from 4 out of the 7 transgenic plants showed strong staining for GUS activity after 2 days in culture, and microspores from 7 out of the 7 transgenic plants showed strong staining for GUS activity after 3 days in culture. $T_4$ microspores from 5 $T_3$ transgenic plants of the same line carrying the pMB351 construct were also isolated and cultured. Microspores from 4 out of these 5 transgenic plants showed strong staining for GUS activity after 2 days in culture.

Similarly, tissues of regenerated $T_1$ plants transformed with the pMB354 construct did not exhibit GUS activity. From about 15 days after flowering, $T_2$ seeds of 144 $T_1$ plants carrying the pMB354 construct stained strongly for GUS activity. $T_2$ microspores from 4 plants of 4 $T_1$ transgenic lines carrying the pMB354 construct were isolated and cultured essentially according to Chen et al. (Plant Breed. 113: 217-221, 1994). $T_2$ microspores from 2 out of these 4 transgenic plants showed strong straining for GUS activity after 2 days in culture, and microspores from 4 out of these 4 transgenic plants showed strong straining for GUS activity after 3 days in culture.

Taken together, the data show that in transgenic plants, the sesame 2S albumin and 11S globulin 5'UTR fragments direct expression in Brassica seeds from about day 15 or day 20 after flowering, respectively. The data also show that in transgenic plants these fragments direct expression in cultured microspores from about day 2 or day 4 in culture, respectively. Tissues that develop from cultured microspores, including embryo tissue, are also expected to exhibit an expression that is directed by these promoters. Therefore, the data suggest that these promoters are suitable for directing the expression of target genes in *Brassica* seeds or embryos.

TABLE 4

Functional Analysis of Sesame Promoters (Stable Expression)

| Constructs | Construct Description | Method of DNA Delivery | $T_1$ tissues [Blue Dots (GUS activity)/ tissue] | $T_2$ Seeds (Transgenic plants with GUS activity/ Total transgenic Plants) | $T_4$ Seeds (Transgenic plants with GUS activity/ Total transgenic Plants) | $T_2$ Microspores (Lines with GUS activity/ Total lines tested) | $T_3$ Microspores (Plants with GUS activity/ Total plants tested) | $T_4$ Microspores (Plants with GUS activity/ Total plants tested |
|---|---|---|---|---|---|---|---|---|
| pMB351 | Glob (p)-GUS-NOS-pMOG800 | *Agrobacterium*-mediated transformation | (0/35) | (35/35) | (13/20) | Not determined | (4/7) after 2 days; (7/7) after 3 days | (4/5) after 2 days |
| pMB354 | Alb (p)-GUS-NOS-pMOG800 | *Agrobacterium*-mediated transformation | (0/159) | (144/144) | Not determined | (2/4) after 2 days; (4/4) after 3 days | Not determined | Not determined |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated nucleic acid having at least 95% sequence identity to the nucleotide sequence set forth in SEQ ID NO:1, wherein said nucleic acid is capable of promoting expression of an operably linked heterologous nucleic acid in a plant cell.

2. A nucleic acid construct comprising the nucleic acid of claim 1 operably linked to a heterologous nucleic acid.

3. A transgenic plant cell containing the nucleic acid construct of claim 2.

4. A transgenic plant containing the nucleic acid construct of claim 2.

5. A method of making a transgenic plant cell, comprising:
introducing the nucleic acid construct of claim 2 into a plant cell; and
selecting a plant cell that contains said nucleic acid construct.

6. A method of making a transgenic plant, comprising introducing the nucleic acid construct of claim 2 into a plant.

7. The isolated nucleic acid of claim 1, wherein said nucleic acid is SEQ ID NO:1.

8. The isolated nucleic acid of claim 1 wherein said nucleic acid has 98% or greater sequence identity to the nucleotide sequence set forth in SEQ ID NO: 1.

9. An isolated nucleic acid comprising a fragment of SEQ ID NO: 1 at least 500 nucleotides in length, wherein said nucleic acid is capable of promoting expression in a plant cell of an operably linked heterologous nucleic acid.

10. The isolated nucleic acid of claim 9, wherein said fragment is at least 1000 nucleotides in length.

11. The isolated nucleic acid of claim 10, wherein said fragment is at least 2000 nucleotides in length.

12. An isolated nucleic acid having a nucleotide sequence selected from the group consisting of a) the nucleotide sequence set forth in SEQ ID NO:1 and b) a fragment of the nucleotide sequence of a) that is at least 500 nucleotides in length and capable of promoting expression of an operably linked heterologous nucleic acid in a plant cell.

* * * * *

UNITED STATES PATENT AND TRADEMARK OFFICE
CERTIFICATE OF CORRECTION

PATENT NO. : 7,750,139 B2
APPLICATION NO. : 10/565898
DATED : July 6, 2010
INVENTOR(S) : Shorrosh et al.

Page 1 of 1

It is certified that error appears in the above-identified patent and that said Letters Patent is hereby corrected as shown below:

In column 4, line 37, delete "govermment's" and insert -- government's --, therefor.

In column 28, line 31, in claim 8, delete "claim 1" and insert -- claim 1, --, therefor.

Signed and Sealed this
Eleventh Day of January, 2011

David J. Kappos
*Director of the United States Patent and Trademark Office*

SEQUENCE LISTING

<160> NUMBER OF SEQ ID NOS: 9

<210> SEQ ID NO 1
<211> LENGTH: 2400
<212> TYPE: DNA
<213> ORGANISM: Sesamum inidicum L.

```
<400> SEQUENCE: 1
ctgaaatcat gtgaactcat aaaatgattt aagaaaaatg aaactaataa gaagatatcc      60
atatgtrtgc cggcattaac actgttcggt gaaggaatt ggagaagaag gaaaragaat     120
ataattcatt ggtgaagaaa ataatgagga acaagttcc acgtggaaaa gaaaataaaa     180
agaatatccg cgaaacttta aatttacggc tgaagaaaac ctgagatcag aaatctcgtg     240
tggaaagtgc cgctcatcgc accaccggaa ttatttcccg gccgatgctg cgtctgcaca     300
tagctgagat tatcatcatt ccatagcttt catcatcaac ggaagaaat attgaaaaag      360 aatcgacttt ggtgaaaaaa caacacacga tacgaagcaa taatacatat gactataaat     420
caaaattcac atatgacgga cagttctaca gaacaaaaag gaatatgtag ccttggaggc     480
aagtcgcaga aaaggcgatg ttaatgccag agttccactc tgccgttctt gacggcataa     540
ttgaagattg aaagggcttt tataataatg ttggccgttg ccctaattcc caaatgggcg     600
cccgcaccgc tgtttggatt cagaatccca atgggaactt ctttcttttt ttcccctcta     660 tttttgtag ttctcccatt tgagaagaaa atgataagtt acatcccgta agttaatttt      720
ttttatgatt ttagtgtcct tgtattttaa ttcaccacat tgcattttat aattttgaaa     780
acttttattt tagttcaaaa tctttaatat cgttaagttt tttataaaaa cgactcgtgt     840
atgaaatgct cttccttaag ttttgagggg aatgaaagtt gtttttgcta gaaattaaat     900
aaaactaaga cttgatattg aaattataat tttcttgaag ttatattata cactgtggcg     960
agttaaaaaa taataaaatc aaaatgacga agatgctaac ttatgggatg taaatgcaat    1020
tctttcatat taatgcaaac tgtaaatatt gcacaaatct ctgtgtcggt tcacctataa    1080
tgtgttgaaa ctttaaaata ttatatttat tttattgaat tcctaatcaa acaaatttgg    1140
tataatcaat ggctcgttcc aaacacaatc actctgttag atatattttg aaacctagaa    1200
aagtatattt ttctttataa tagatattat agataacaaa ctataagttt cagaataatg    1260
ctagtagtag tggtgattac caaatctgaa tatgaagata gaactatatt tgcaacataa    1320
ttttgatagt ataaaattat attcatgaca aagtcttagg agtttcattt atttgatttt    1380
gggagttcaa ttacaaataa caagtgagga ggggtgtgat gaatggatca aatttgggtt    1440
gttgttgggc tccatccact tgaaaccctg tcatccattc tattgacctt ttgaagtgat    1500
tgtagttgtt gtgctttagt aggcacttat cacatgccat tgagttcaaa aagagaaaaa    1560
ttgcgtcaca tgttgtccat gtctacaatg ctttttataag ctaaattgaa tgggttgata    1620
aacaagttag actagaaatt aatggatttt tcctttcgtt ttatagggga ttgaattttc    1680
tattgtatat tacttttatg agtataattt gtctttgaaa taaattaggt aatgtaatat    1740
ttgtagttat gttaaatgaa ataaaagata taataatctt taaaataatt tttttgctta    1800
tgttgttaat gatgcaactt tattcttctt tttttataag cacacaccca attcaaaccc    1860
aagatctttg atatgcagtt tgagcccaa actgtggaac tgtccttgga gctaaagatg     1920
catcaaggga acttaaacaa gagttagagg tataattgtt gagttgtaat atgctaataa    1980
ctcattattt tagtttgtct cctccatgga taaggatgtc ttttatgacc agctcaattt    2040
ctgttaattg gccattaaag tttccttag cactrgttca gacacttacg agaaagagaa      2100
acattttgtg ttagaggaac taatattaat taaactagat ccaaaagaga agttctaaaa    2160
aattcaagtc ctctgttttg gcaacatctg catgtagaca tcgatgtgga agctcgaaaa    2220
cgccagcctc agtcccctca gcaaaacccg tccacctatc tcttccatca atcaacacgt    2280
```

```
aaaagccatg cacccgcaca aaaccactat aaatcccct  tcaaaccct  ccaccattct     2340 cacaccactg taaactcatc tactcctttc ctacatataa atctcagttc aagaacaacc     2400
```

<210> SEQ ID NO 2
<211> LENGTH: 2947
<212> TYPE: DNA
<213> ORGANISM: Sesamum inidicum L.

<400> SEQUENCE: 2

```
caataagaag tcctctcctc tccgagctaa atcctttgta taaaaaagtg cctgttcttg       60
ttcatgatgg aaagccgctg tctgattcct ccattatact ggagtacgtc gatcagaaat      120
ggaggtccaa ccccttgttc cccgacgatc cctaccaaag agcccaagcc cacttatggg      180
ctagatttgc cgatgagaag gtacatggga taaaatactt ttgcttctat atatatttga      240
tgactaataa aattacgtga attcttattc ggtttagaaa atttcatgcc gtagagataa      300
tatgtgatcc taatcataca atgtaatgac accagataac tactctgagc atataaattc      360
cgttgatcct caggttcttg aatcagcatg gcttgctctc tgttcggaag gaaagacgca      420
ggagagagca gtgaaacaag ccattgagaa cctggaacat gtcgaagaga agctgaaagg      480
gaagaggttc ttcggagggg acataattgg gcatgtggac ctaatgatgg gcttcgtttc      540
ctacatgttg cctgtttggg aagaggttgc cggagtgaaa atcctggatc ccacacaaatt     600 cccagctata gctgcctgga cgaataattt cctcaatcat gaagccatca aggctgaata      660
tttgccaccc actgctgaga ccttcaccta tttccagtgg cgacgaaaag aattaattcc      720
tgtctatgcc tcttatggac agtagatggt gtaatcaaca aaagtcggaa tagagaatct      780
gaggctgtat tagaggataa atcgaagtcc aattcattgg actgagtacg aggtttttaa      840
gcgttgtaat ttcttgaagc agtacatctg cctgtattag tacagaggat ccgtgcacca      900
aaaatcttat ccacccaaaa agatctcctt tttatataaa tcttgtacgc cccgtctttc      960
ttattataat tgttcgttta gaattttcag tattttggga aagtatttag tattgtttgt     1020
tgtcagttta aaattttctt agttactaaa ttattttcaa tattttactt taatttggtg     1080
tgtttatata atttcatatt tattttgagat ttatgatcca ttattataat catttaatta    1140
taaatatatg aagtttaata agtatttagc ccttacgact tacatattca tatggctttt     1200
tatagttaaa tttatcatga ttttataagt tttttattagg ccacttaact ttttgtaatt    1260
gccaaattcg ttacaactac tttgtcatta cctttttact tcagcacgtt gagaagggaa     1320
gccttcgtat gatttttcaa agtacttctt acattttatc tagtgtttga gagttttggc     1380
aacgtgacta tggattggtc attgtctcct cattctcatg cctagagtca tagccaatca     1440
ttaatacacc aagtaggaag tcaatcataa ccttaagaaa gtgacaagac tttattcgaa     1500
attaaattat taatatttga gcacaaacta taaaaaataa aatttatttt ttgagtaaaa     1560
gtattagata atatttttat taaatagtaa attaatttta aaattaaaat tatttacact     1620
cgagataaat tgcagcagct attaattttt ttttaaattg aatttttatt ataaaatttt     1680
tacaaatatt ttaataaact tcgaccataa attataagaa ataaaaattt aaaaactaaa     1740 gaattatat tttaatataa ataaaaaata gtttataact tataattata tttattttta     1800
gataacttct aacatatttt aattattttt aaaattacat attattttatt ctaaaaaaat    1860 ttaataaact ttgacaaaga aaagtaaaa aataaaattt tattttattt ctacaattta      1920 tctcacaatgt aaataattat aatttaaaaa ttatttaata aaaagtttat ctaatacttt    1980
tattcaaaaa taaattctac tttttatagt ttgtgctcac atattaatat attttttagac   2040
```

```
caaataataa tttaatttca aaaatagtat aatagatcct agaaattatc taaaaataaa      2100
ataattataa ttttagaacc attttattat atatattaaa ataattttt ttaatatttt      2160 ctatttttgt aaaaataaaa attcttatag tttgtggcca aagttggtca aaatattttt      2220
ttttctttta atggtactta aaaaacacgt ttctttatt ttttggtacc tttaaatagg      2280
tatttgaagt tcaaagtcat gttagtcaat agaagtttac taccgttaac ggccacgtgc      2340
gggacacatg gcctctgttg ttaacttggg acaaaaagt atgttttttg tgttttatag      2400
taccaaaagt gacacttgcc acaattatgg tacccaaaat aaaatcaact ttttttaacg      2460
gaatcaaaaa aaaaaaattt tgcccttaca taatatatgt actaatcaac ggattgaatt      2520
ttctattgta atattcattt cattttctat ttcgttcaac atatacaatt atgtatattt      2580
gaacgaaatc atatatttta ttttgaaaaa taaaaaaaaa ttaacacatg ctatgtatat      2640
attgattgta ataaaaaata aaataattaa aatttgcaac aaatgcaatc caaccaaaca      2700
taatcgccac atacccatta ggtgtaagca gagcagcatt tccatacatg caacctcatg      2760
atgatcataa caaaacaaaa gcccatgcac aatagatacc gccaaatgtc gctcgttttct      2820 caccatctca cactcgacgt gtcgacctca acccaccaat ttcaactata aatccccacc      2880
cttctctatt ccccgcttca catccatcat cagccccctc aaactactaa tcccagcacc      2940
tccaaac                                                              2947

<210> SEQ ID NO 3
<211> LENGTH: 32
<212> TYPE: DNA
<213> ORGANISM: Artificial Sequence
<220> FEATURE:
<223> OTHER INFORMATION: Primer

<400> SEQUENCE: 3
gtcgacctga aatcatgtga actcataaaa tg                                     32

<210> SEQ ID NO 4
<211> LENGTH: 33
<212> TYPE: DNA
<213> ORGANISM: Artificial Sequence
<220> FEATURE:
<223> OTHER INFORMATION: Primer

<400> SEQUENCE: 4
ggatccggtt gttcttgaac tgagatttat atg                                    33

<210> SEQ ID NO 5
<211> LENGTH: 29
<212> TYPE: DNA
<213> ORGANISM: Artificial Sequence
<220> FEATURE:
<223> OTHER INFORMATION: Primer

<400> SEQUENCE: 5
aagcttcaat aagaagtcct ctcctctcc                                         29

<210> SEQ ID NO 6
<211> LENGTH: 29
<212> TYPE: DNA
<213> ORGANISM: Artificial Sequence
<220> FEATURE:
<223> OTHER INFORMATION: Primer

<400> SEQUENCE: 6
```

-continued

```
ctagagtttg gaggtgctgg gattagtag                                29

<210> SEQ ID NO 7
<211> LENGTH: 37
<212> TYPE: DNA
<213> ORGANISM: Sesamum inidicum L.

<400> SEQUENCE: 7
tcagaaatct cgtgtggaaa gtgccgctca tcgcacc                        37

<210> SEQ ID NO 8
<211> LENGTH: 12
<212> TYPE: DNA
<213> ORGANISM: Sesamum inidicum L.

<400> SEQUENCE: 8
taatattaat ta                                                   12

<210> SEQ ID NO 9
<211> LENGTH: 12
<212> TYPE: DNA
<213> ORGANISM: Sesamum inidicum L.

<400> SEQUENCE: 9
aatattttta tt                                                   12
```